United States Patent
Zhang et al.

(10) Patent No.: US 10,513,740 B2
(45) Date of Patent: Dec. 24, 2019

(54) PRIMER PAIR, KIT AND METHOD FOR DETECTING ANAPLASMA PLATYS

(71) Applicant: Delta Electronics Int'l (Singapore) Pte Ltd, Singapore (SG)

(72) Inventors: Yong Zhang, Singapore (SG); Chih-Yu Chao, Singapore (SG)

(73) Assignee: DELTA ELECTRONICS INT'L (SINGAPORE) PTE LTD, Singapore (SG)

(*) Notice: Subject to any disclaimer, the term of this patent is extended or adjusted under 35 U.S.C. 154(b) by 23 days.

(21) Appl. No.: 15/678,732

(22) Filed: Aug. 16, 2017

(65) Prior Publication Data

US 2018/0073058 A1 Mar. 15, 2018

Related U.S. Application Data

(60) Provisional application No. 62/393,204, filed on Sep. 12, 2016.

(30) Foreign Application Priority Data

Aug. 3, 2017 (SG) .......................... 10201706362X

(51) Int. Cl.
| | | |
|---|---|---|
| *C07H 21/04* | (2006.01) | |
| *C12Q 1/68* | (2018.01) | |
| *C12Q 1/689* | (2018.01) | |
| *C07K 16/12* | (2006.01) | |
| *G01N 33/569* | (2006.01) | |

(52) U.S. Cl.
CPC .......... *C12Q 1/689* (2013.01); *C07K 16/1246* (2013.01); *G01N 33/56911* (2013.01); *C12Q 2600/16* (2013.01); *G01N 2333/29* (2013.01)

(58) Field of Classification Search
None
See application file for complete search history.

(56) References Cited

U.S. PATENT DOCUMENTS

| 7,507,789 B2 | 3/2009 | Beall et al. |
| 7,906,296 B2 | 3/2011 | Beall et al. |
| 2014/0162256 A1 | 6/2014 | Rikihisa |

FOREIGN PATENT DOCUMENTS

WO  WO-2014197607 A1 * 12/2014 ......... G01N 33/5308

OTHER PUBLICATIONS

NEB catalog (1998/1999), pp. 121, 284. (Year: 1998).*
Peleg et al. (Veterinary Parasitology, vol. 173, pp. 292-299, 2010) (Year: 2010).*
Rotondano et al. (The Scientific World Journal, vol. 2012, Article ID 605743, Jul. 2012) (Year: 2012).*
Da Silva et al. (J. of Veterinary Diagnostic Investigation, vol. 28, No. 5, pp. 529-535, 2016). (Year: 2016).*
Ramos RA et al., Vet Parasitol. Sep. 15, 2014; 205(1-2):285-8.
Sirigireddy KR et al. , J Mol Diagn. May 2005; 7(2):308-16.
NCBI GenBank: U54806.1.

* cited by examiner

*Primary Examiner* — Jeanine A Goldberg
(74) *Attorney, Agent, or Firm* — Kirton McConkie; Evan R. Witt

(57) ABSTRACT

Primer pair, kit and method for detecting *Anaplasma platys* are disclosed. The primer pair includes a forward primer and a reverse primer, and the kit includes the primer pair and a probe. The forward primer has a sequence of SEQ ID NO: 1, the reverse primer has a sequence of SEQ ID NO: 2, and the probe has a sequence of SEQ ID NO: 3.

3 Claims, 4 Drawing Sheets
Specification includes a Sequence Listing.

1    TTGTCGTAGC TTGCTATGAT AACGGTTAGT GGCAGACGGG TGAGTAATGC ATAGGAATCT
61   ACCTAGTAGT ATGGGATAGC CACTAGAAAT GGTGGGTAAT ACTGTATAAT CCCTGCGGGG
121  GAAAGATTTA TCGCTATTAG ATGAG    - SEQ ID NO: 4

FIG. 1

| Name | Sequence |
|---|---|
| Forward Primer | 5'-GTCGTAGCTTGCTATGATA-3'   (SEQ ID NO: 1) |
| Reverse Primer | 5'-CCATACTACTAGGTAGATTCC-3'   (SEQ ID NO: 2) |
| Probe | 5'-CTCACCCGTCTGCCACTAAC-3'   (SEQ ID NO: 3) |

FIG. 2

PRIMER PAIR, KIT AND METHOD FOR DETECTING ANAPLASMA PLATYS

CROSS-REFERENCE TO RELATED APPLICATION

This application claims the benefit of U.S. Provisional Application Ser. No. 62/393,204 filed on Sep. 12, 2016, and claims the priority to Singapore Patent Application No. 10201706362X filed on Aug. 3, 2017, the entire contents of which are incorporated herein by reference for all purposes.

FIELD OF THE INVENTION

The present invention relates to a quick diagnosis of *Anaplasma platys*, and more particularly to primer pair, kit and method for detecting *Anaplasma platys*.

BACKGROUND OF THE INVENTION

*Anaplasma platys* (former *Ehrlichia platys*) causes canine cyclic thrombocytopenia in tropical and warm regions of the world, like the Mediterranean, Asia, Middle East, Africa, Australia, and the USA. Canine anaplasmosis is a widespread disease and therefore called a "canine emerging disease". The Brown Dog tick (*Rhipicephalus sanguineus*) and *Dermacentor* spp. are thought to transmit the pathogen. *Anaplasma platys* are the only *rickettsia* known to infect platelets. The organisms appear as round, oval or bean shaped blue cell inclusions in platelets and range from 0.35 to 1.25 µm in diameter.

Signs of *Anaplasma platys* infection include fever, anorexia, lethargy, primary hemostatic disorders as the pathogen destroys platelet cells of the host, mild anemia, and lymphadenomegaly. Bacteraemia and subsequent thrombocytopenic episodes (with platelet counts below 20,000/µl) recur at 1 to 2 week intervals. Co-infection with *E. canis* may lead to severe diseases.

Generally, the methods employed for *Anaplasma platys* diagnosis includes blood smear, serologic diagnosis and molecular diagnosis, but each method has some limitations.

A diagnosis of *Anaplasma platys* may be made by detecting organisms within platelets on stained blood films or buffy coat smears (e.g. Giemsa or Diff-Quik). Due to cyclic parasitemia the pathogen could either be absent or present in very low numbers. Thus this method is not reliable, and shows low sensitivity and time consuming.

Serologic diagnosis may be helpful in identifying the presence of antibodies to *Anaplasma platys*, but may not detect early infections during the acute phase of disease. The limitation of serologic diagnosis is cross-reaction, and the cross-reaction among the *Ehrlichia* spp. and *Anaplasma* spp. is commonly recognized. Moreover, it is difficult to differentiate between post exposure and present infection.

The most current and best way to diagnose *Anaplasma platys* is molecular diagnosis, especially by polymerase chain reaction (PCR) testing. PCR, which is more sensitive and specific technique, offers an alternative approach for the diagnosis of anaplasmosis. An 16S rRNA gene sequence has been helpful in identifying species of *Anaplasma*. For example, the VetPCR *A. platys* Detection Kit provided by BioinGentech is used to diagnose *Anaplasma platys* infection, and it is a very fast, accurate and reliable technique. However, end-point PCR detection method, i.e. gel electrophoresis, should be combined with this diagnostic kit, and the whole procedure will take 3 hours, which is quite labor and time consuming.

Therefore, there is a need of providing an *Anaplasma platys* diagnosis in order to overcome the above drawbacks.

SUMMARY OF THE INVENTION

An object of the present invention is to provide a primer pair for detecting *Anaplasma platys* with high sensitivity and high specificity in order to rapidly and accurately diagnose *Anaplasma platys* infection.

Another object of the present invention is to provide a kit for detecting *Anaplasma platys* with high sensitivity and high specificity in order to rapidly and accurately diagnose *Anaplasma platys* infection.

An additional object of the present invention is to provide a method for detecting *Anaplasma platys* with high sensitivity and high specificity in order to rapidly and accurately diagnose *Anaplasma platys* infection.

According to an aspect of the present invention, there is provided a primer pair for detecting *Anaplasma platys*, comprising a forward primer having a sequence of 5'-GTCGTAGCTTGCTATGATA-3' (SEQ ID NO: 1) and a reverse primer having a sequence of 5'-CCATACTACTAGGTAGATTCC-3' (SEQ ID NO: 2). The forward primer and the reverse primer are used for real-time polymerase chain reaction.

According to another aspect of the present invention, there is provided a kit for detecting *Anaplasma platys*, comprising a forward primer having a sequence of 5'-GTCGTAGCTTGCTATGATA-3 (SEQ ID NO: 1)', a reverse primer having a sequence of 5'-CCATACTACTAGGTAGATTCC-3' (SEQ ID NO: 2) and a probe having a sequence of 5'-CTCACCCGTCTGCCACTAAC-3' (SEQ ID NO: 3). The forward primer, the reverse primer and the probe are used for real-time polymerase chain reaction. The probe is labeled with a 5'-reporter dye and a 3'-quencher.

According to an additional aspect of the present invention, there is provided a method for detecting *Anaplasma platys*, the method comprising amplifying nucleic acid from *Anaplasma* platys using real-time polymerase chain reaction with a forward primer having a sequence of 5'-GTCGTAGCTTGCTATGATA-3' (SEQ ID NO: 1), a reverse primer having a sequence of 5'-CCATACTACTAGGTAGATTCC-3' (SEQ ID NO: 2) and a probe having a sequence of 5'-CTCACCCGTCTGCCACTAAC-3' (SEQ ID NO: 3). The probe is labeled with a 5'-reporter dye and a 3'-quencher.

The above objects and advantages of the present invention become more readily apparent to those ordinarily skilled in the art after reviewing the following detailed description and accompanying drawings, in which:

BRIEF DESCRIPTION OF THE DRAWINGS

FIG. 1 shows the corresponding positions of the forward primer, the reverse primer and the probe on the sequence of the 16S rRNA gene;

FIG. 2 shows the DNA sequences of the forward primer, the reverse primer and the probe.

DETAILED DESCRIPTION OF THE PREFERRED EMBODIMENT

Figure 3A:
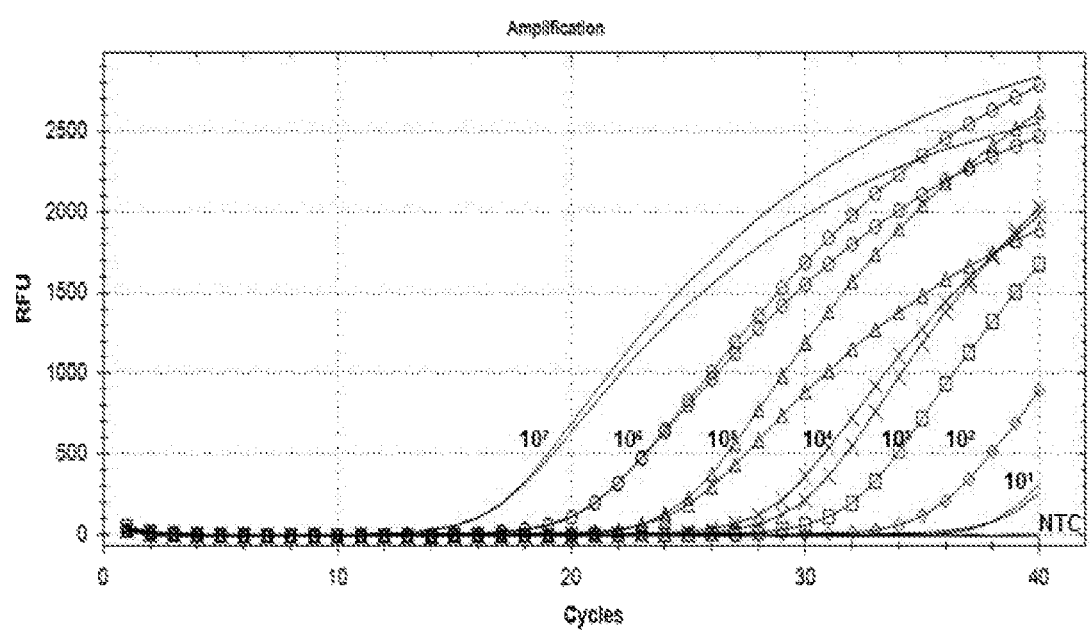
FIGS. 3A and 3B show the analysis of the amplification of the real-time PCR assay.

The present invention will now be described more specifically with reference to the following embodiments. It is to be noted that the following descriptions of preferred embodiments of this invention are presented herein for purpose of illustration and description only; it is not intended to be exhaustive or to be limited to the precise form disclosed.

The present invention utilizes real-time polymerase chain reaction (Real-time PCR), also called quantitative polymerase chain reaction (Q-PCR), with probe-based detection for detecting *Anaplasma platys*. In Real-time PCR, the specific forward and reverse primers and probe hybridize to the DNA target of *Anaplasma platys*, wherein the probe is labeled with a 5'-reporter dye and a 3'-quencher. During PCR amplification, the probe is cleaved and the reporter dye and quencher are separated, so that the resulting increase in fluorescence can be detected. In an embodiment, the reporter dye is FAM fluorescence, and the quencher is BHQ1 group.

The DNA target for this assay is a variable region of the 16S rRNA gene (GenBank accession number: KP939260.1) that contains sequence that is species-specific for *Anaplasma platys*. PCR primers and probe are designed using Primer3 and chosen on the basis of GC content and lack of hairpin structures. FIG. 1 shows the corresponding positions of the forward primer, the reverse primer and the probe on the sequence of the variable region of the 16S rRNA gene (SEQ ID NO: 4). As shown in FIG. 1, the forward primer starts at position 3, the probe starts at position 44, and the reverse primer starts at position 74. This primers and probe combination is predicted to amplify the DNA of *Anaplasma platys* strains with an amplicon size of 72-bp. FIG. 2 shows the DNA sequences of the forward primer, the reverse primer and the probe, wherein the forward primer (SEQ ID NO: 1) includes 19-mer, the reverse primer (SEQ ID NO: 2) includes 21-mer, and the probe (SEQ ID NO: 3) includes 20-mer.

To ascertain the specificity of the PCR primers and the probe for *Anaplasma platys*, the primer pair, including the forward primer and the reverse primer, and the probe are checked by Primer-BLAST from NCBI, and the blast result shows that no other similar species have 100% same fragment compare to the primer pair and the probe of the present invention. The result demonstrates that the specificity of the primer pair and the probe is quite high, and the primer pair and the probe can be only used to amplify and detect the 16S rRNA gene of *Anaplasma platys*.

Therefore, the present invention provides a primer pair for detecting *Anaplasma* platys, comprising a forward primer having a sequence of 5 '-GTCGTAGCTTGCTATGATA-3' (SEQ ID NO: 1) and a reverse primer having a sequence of 5'-CCATACTACTAGGTAGATTCC-3' (SEQ ID NO: 2). The present invention also provides a kit for detecting *Anaplasma platys*, comprising a forward primer having a sequence of 5'-GTCGTAGCTTGCTATGATA-3' (SEQ ID NO: 1), a reverse primer having a sequence of 5'-CCATACTACTAGGTAGATTCC-3' (SEQ ID NO: 2) and a probe having a sequence of 5'-CTCACCCGTCTGCCACTAAC-3' (SEQ ID NO: 3). On the other hand, the present invention also provides a method for detecting *Anaplasma platys*, the method comprising amplifying nucleic acid from *Anaplasma platys* using real-time polymerase chain reaction with a forward primer having a sequence of 5'-GTCGTAGCTTGCTATGATA-3' (SEQ ID NO: 1), a reverse primer having a sequence of 5'-CCATACTACTAGGTAGATTCC-3' (SEQ ID NO: 2) and a probe having a sequence of 5'-CTCACCCGTCTGCCACTAAC-3' (SEQ ID NO: 3).

In some other embodiments, since the primer pair of the present invention is specific to *Anaplasma platys*, all the sequence located between the forward primer and the reverse primer may be used as the probe sequence, and thus, the probe sequence is not limited to the aforesaid sequence. Further, the probe can be designed to hybridize to any strand of the DNA, so both the complementary sequences at the same location can be used as the probe sequence. Therefore, the complementary sequence of the aforesaid probe sequence may also be used as the probe sequence for detecting *Anaplasma platys*.

The following describes an example of the method for detecting *Anaplasma platys* of the present invention.

First, DNA is extracted from 200 µl of EDTA-preserved whole blood using the QIAamp DNA blood Mini kit for blood protocol (Qiagen) and eluted in 100 µl of elution buffer. Then the real-time PCR assay is performed on the Bio-Rad real-time PCR machine (CFX96). The PCR reaction mixture includes 10 µl of KAPA Fast probe universal master mix, 250 nM of forward and reverse primers and 250 nM of probe, wherein the forward primer has a sequence of 5'-GTCGTAGCTTGCTATGATA-3' (SEQ ID NO: 1), the reverse primer has a sequence of 5'-CCATACTACTAGGTAGATTCC-3' (SEQ ID NO: 2) and the probe has a sequence of 5'-CTCACCCGTCTGCCACTAAC-3' (SEQ ID NO: 3). 3 µl extracted DNA template is added to each reaction in a total volume of 20 µl. Cycling conditions are as follows: 95° C. for 3 min, followed by 40 cycles of denaturation at 95° C. for 3 sec, and annealing/extension at 60° C. for 20 sec.

An *Anaplasma platys*-positive control is constructed by cloning the partial 16S rRNA gene fragment into a vector (RBC Cloning System). A series of seven 10-fold dilutions are prepared from this recombinant plasmid DNA (10, $10^2$, $10^3$, $10^4$, $10^5$, $10^6$ and $10^7$ copies/µl). The dilution series are analyzed in duplicate to determine the lower limit of *Anaplasma platys* DNA detection and the linearity and efficiency of amplification of this real-time PCR assay.

Figure 3B:
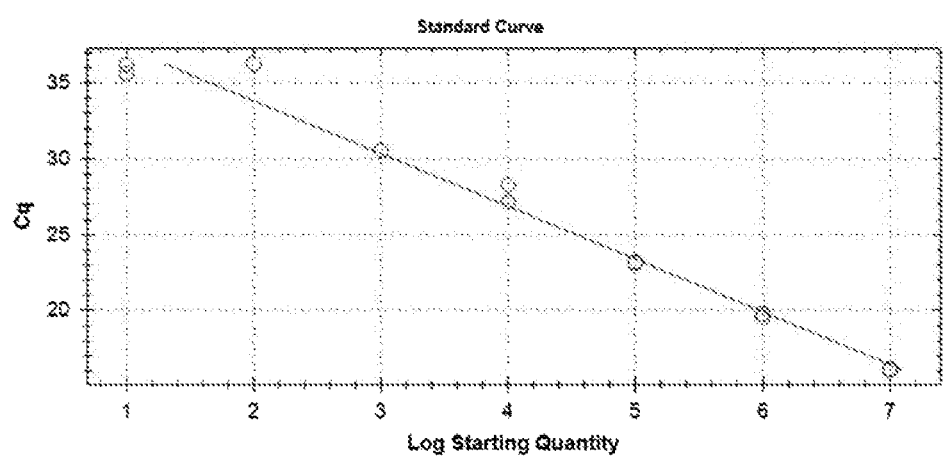

FIGS. 3A and 3B show the analysis of the amplification of the real-time PCR assay. FIG. 3A shows the amplification curve of different copies of plasmid samples, which reveals that the assay has high sensitivity. FIG. 3B shows the assay has good linearity with an $R^2$ of 0.98, which is very close to the theoretical optimum of 1.0. Therefore, the assay could be expanded as a quantitative assay to estimate gene copy number in clinical samples.

In conclusion, the present invention provides a method for detecting *Anaplasma platys* using real-time PCR with specific primer pair and probe. The method of the present invention has advantage of high sensitivity, and should allow the detection of low *Anaplasma platys* in subclinically infected cases. Moreover, diagnosis in early stage or acute phase is very critical for *Anaplasma platys* treatment; some studies show that when dogs are treated in the acute phase of anaplasmosis, they improve quickly, within 24-48 hours, and their prognosis is good when the whole courses of therapy are administered. The method of the present invention further has advantage of high specificity, which is able to specifically differentiate *Anaplasma platys* with other tick-borne pathogens and is very helpful for vets to choose the optimal treatment program. In addition, in recurrent disease after treatment or failure after treatment, the method of the present invention could determine if the original diagnosis was incorrect, so as to reduce risk of transfusion transmission by testing blood donors.

While the invention has been described in terms of what is presently considered to be the most practical and preferred embodiments, it is to be understood that the invention needs not be limited to the disclosed embodiment. On the contrary, it is intended to cover various modifications and similar arrangements included within the spirit and scope of the appended claims which are to be accorded with the broadest interpretation so as to encompass all such modifications and similar structures.

What is claimed is:

1. A method for detecting *Anaplasma platys*, the method comprising amplifying nucleic acid from *Anaplasma platys* using real-time polymerase chain reaction with a forward primer consisting of a sequence of 5'-GTCGTAGCTTGC-TATGATA-3' (SEQ ID NO: 1) and a reverse primer consisting of a sequence of 5'-CCATACTACTAGGTAGAT-TCC-3' (SEQ ID NO: 2).

2. The method according to claim 1 wherein a probe consisting of a sequence of 5'-CTCACCCGTCTGC-CACTAAC-3' (SEQ ID NO: 3) is used for the real-time polymerase chain reaction.

3. The method according to claim 2 wherein the probe is labeled with a 5'-reporter dye and a 3'-quencher.

* * * * *

SEQUENCE LISTING

<160> NUMBER OF SEQ ID NOS: 4

<210> SEQ ID NO 1
<211> LENGTH: 19
<212> TYPE: DNA
<213> ORGANISM: Artificial Sequence
<220> FEATURE:
<223> OTHER INFORMATION: Synthetically generated primer

<400> SEQUENCE: 1
gtcgtagctt gctatgata                                          19

<210> SEQ ID NO 2
<211> LENGTH: 21
<212> TYPE: DNA
<213> ORGANISM: Artificial Sequence
<220> FEATURE:
<223> OTHER INFORMATION: Synthetically generated primer

<400> SEQUENCE: 2
ccatactact aggtagattc c                                       21

<210> SEQ ID NO 3
<211> LENGTH: 20
<212> TYPE: DNA
<213> ORGANISM: Artificial Sequence
<220> FEATURE:
<223> OTHER INFORMATION: Synthetically generated probe

<400> SEQUENCE: 3
ctcacccgtc tgccactaac                                         20

<210> SEQ ID NO 4
<211> LENGTH: 145
<212> TYPE: DNA
<213> ORGANISM: Anaplasma platys

<400> SEQUENCE: 4
ttgtcgtagc ttgctatgat aacggttagt ggcagacggg tgagtaatgc ataggaatct     60
acctagtagt atgggatagc cactagaaat ggtgggtaat actgtataat ccctgcgggg    120
gaaagattta tcgctattag atgag                                         145